(12) United States Patent
Lima

(10) Patent No.: US 6,503,547 B1
(45) Date of Patent: Jan. 7, 2003

(54) METHOD FOR DIFFUSING OZONE IN A CLOSED ENVIRONMENT

(75) Inventor: Carles Lima, Santiago (CL)

(73) Assignee: Grupo Interozone (CL)

( * ) Notice: Subject to any disclaimer, the term of this patent is extended or adjusted under 35 U.S.C. 154(b) by 0 days.

(21) Appl. No.: 09/443,646

(22) Filed: Nov. 18, 1999

(51) Int. Cl.⁷ .......................... A23L 3/26; A23L 3/3409
(52) U.S. Cl. ........................ 426/231; 426/335; 422/5; 422/124; 422/186.07
(58) Field of Search ................. 426/231, 335; 422/5, 124, 186.07, 907

(56) References Cited

U.S. PATENT DOCUMENTS

| | | | | |
|---|---|---|---|---|
| 4,309,388 A | * | 1/1982 | Tenney et al. ............... | 422/304 |
| 4,549,477 A | * | 10/1985 | McCabe, Jr. .................. | 99/477 |
| 4,849,237 A | * | 7/1989 | Hurst .......................... | 426/332 |
| 5,403,602 A | * | 4/1995 | Endico ........................ | 426/231 |
| 5,514,345 A | * | 5/1996 | Garbutt et al. ............... | 422/124 |
| 5,573,733 A | * | 11/1996 | Salama ................... | 422/186.18 |
| 5,766,560 A | * | 6/1998 | Cole ...................... | 422/186.18 |
| 6,066,348 A | * | 5/2000 | Yuan et al. .................. | 426/236 |

FOREIGN PATENT DOCUMENTS

| | | | |
|---|---|---|---|
| JP | 2000-175667 | * | 6/2000 |
| WO | WO 90/02572 | * | 3/1990 |

\* cited by examiner

Primary Examiner—Nina Bhat
(74) Attorney, Agent, or Firm—Knobbe, Martens, Olson & Bear LLP.

(57) ABSTRACT

A method of preserving natural perishable products by dispersing ozone throughout a substantially closed room containing the natural perishable products is taught wherein the ozone is generated from the oxygen in the air inside the substantially closed room.

11 Claims, 2 Drawing Sheets

METHOD FOR DIFFUSING OZONE IN A CLOSED ENVIRONMENT

FIELD OF THE INVENTION

The present invention relates to a method of preserving natural perishable products by dispersing ozone throughout a substantially closed room containing said natural perishable products.

BACKGROUND OF THE INVENTION

The purification of environments can be achieved through the use of ozone. Ozone has been used to purify air conditioning systems in buildings and to sanitize warehouses where products are stored. Despite its widespread use, this basic technique has the disadvantage of accumulating more ozone than is necessary in the treated environment, requiring the elimination of the excess ozone. Several different improvements in this method have been made in an attempt to control the levels of ozone in the environment being treated. One such improvement provides high initial levels of ozone to the environment sufficient to produce the desired bacteriostatic or bacteriocidal effect. Later the levels of ozone are reduced so that they do not produce harmful effects to the products being treated or to humans.

The majority of the known systems for purifying substantially closed areas with ozone are based on an ozone generator that utilizes a source of concentrated oxygen. When ozone is generated from a source of concentrated oxygen, the level of oxygen in the enclosure rises along with the level of ozone. The increase in oxygen levels is due to the breakdown of ozone into new molecules of oxygen. An increase in the level of oxygen in enclosures containing natural perishable products enhances cellular metabolism and thus is detrimental to the storage of the perishable products.

SUMMARY OF THE INVENTION

The method of the present invention is rather simple, but produces unexpected beneficial effects compared to the state of the art methods. The method of the present invention is applied to substantially closed rooms or rooms with a controlled atmosphere. A substantially closed room is a room that is closed but not necessarily air-tight. The substantially closed room may have a closed circuit air conditioning system, such as a cooling system, for the preservation of perishable natural products. A known ozone generator is placed in proximity with the substantially closed room such that the ozone generator can draw in air from the substantially closed room and liberate ozone into the substantially closed room. The generated ozone may be delivered into the substantially closed room through the action of the air conditioning system. The ozone thus enters the atmosphere of the closed room along with the conditioned air. In this way the design characteristics of the air conditioning system are taken advantage of so that the ozone is efficiently distributed throughout the volume of the room.

In contrast to known ozonation systems, the present invention utilizes oxygen from the air of the room in which the purification treatment is being applied. Because the present invention converts oxygen from the air into ozone, no increase in oxygen levels is observed in the closed room. Rather, the gaseous equilibrium is shifted so that there is a decrease in the level of oxygen in the enclosure. Thus when the method of the present invention is applied, the oxygen levels in the enclosure tend to go down initially and then return partially as breakdown products of ozone generate new molecules of oxygen. This overall reduction in oxygen levels helps with the preservation of perishable natural products stored in the closed room by reducing cellular metabolism.

Additionally, the method of the invention can be used with sensors for temperature, humidity and ozone concentration. This allows the user to optimize the level of ozone generation depending on the special characteristics of the perishable food products. This can be done manually or automatically. However, dynamic control systems are not needed with the present method.

DETAILED DESCRIPTION OF THE PREFERRED EMBODIMENTS

Figure 1:
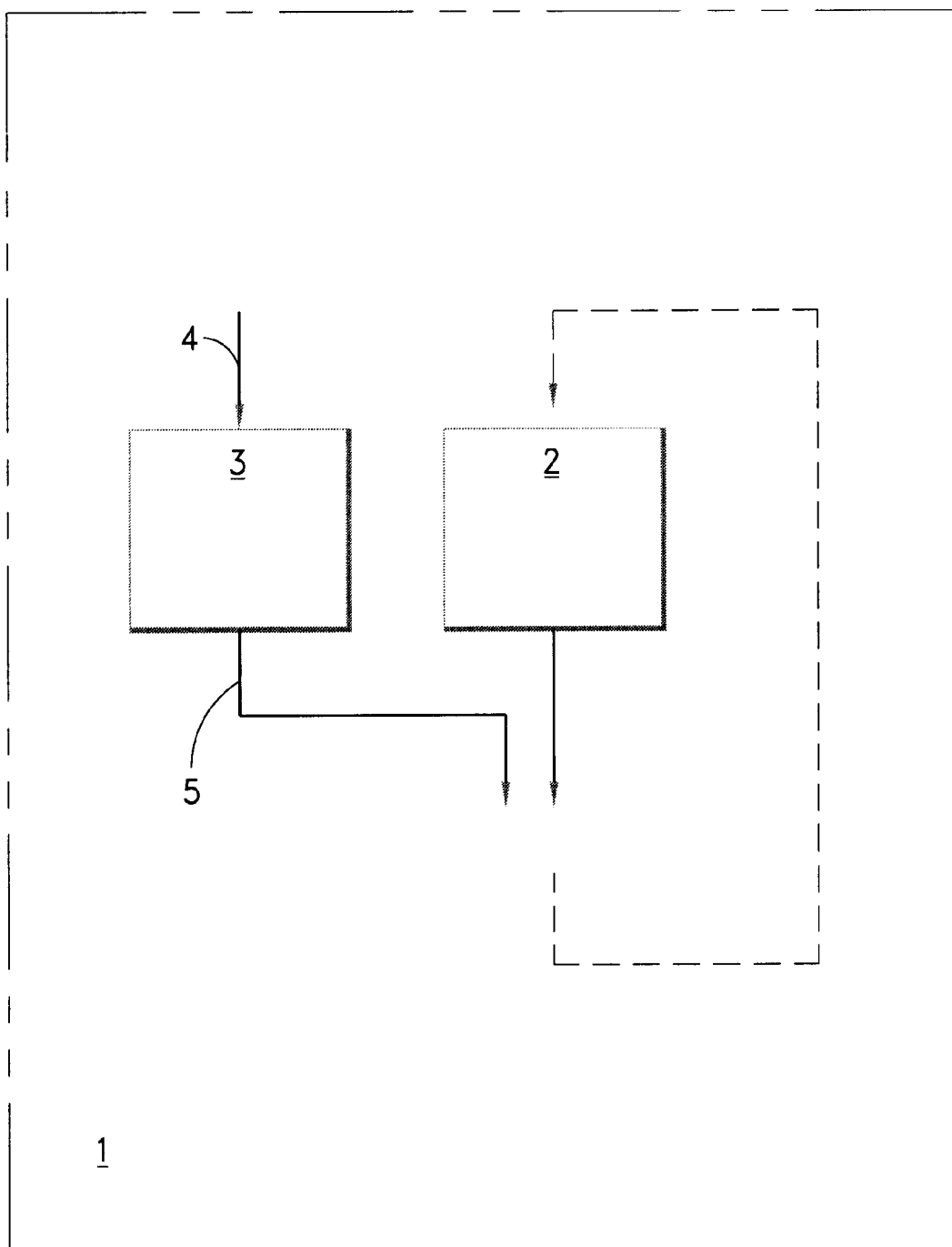
FIG. 1 shows a block diagram of the method of the preferred embodiment of the invention.

Natural perishable products are subject to spoilage as a result of decay and the growth of microorganisms. The method of the present invention reduces these problems and thus increases the length of time that natural perishable products can be stored without spoiling. As is shown in FIG. 1, the preferred embodiment of the method of the present invention makes use of a substantially closed room 1 in which natural perishable products are stored. The substantially closed room 1 has a closed circuit air conditioning system 2. The air conditioning system 2 may comprise heating and cooling capabilities, as well as humidification systems. In addition, the air condition system may comprise a network of vents that allow for the conditioning of the air in the substantially closed room 1 without taking in fresh air from outside. Ozone generating means 3 are provided with an air entrance 4 and an ozone exit 5. The entrance of air into the ozone generating means 3 can be mediated through a forced suction or by natural suction. When mediated through a forced suction, the ozone generating means 3 contains a turbine which draws in air through a filter and sends air out the other side. The ozone generated by the ozone generating means 3 is liberated through the ozone exits 5 which are located immediately adjacent to the vent of the air conditioning system, such that the ozone produced will be distributed throughout the substantially closed room 1.

The ozone generating means 3 is designed to run constantly to maintain the appropriate level of ozone in the substantially closed room 1. However, one skilled in the art will recognize that the appropriate level of ozone may also be obtained by turning the ozone generating means 3 on and off periodically. If the substantially closed room 1 is empty, less ozone production will be required than if the substantially closed room 1 is full. If the substantially closed room 1 is full, the ozone generating means 3 may have to run at full capacity to generate the desired ozone concentration.

In the preferred embodiment of the invention, no oxygen from the outside is injected into the substantially closed room 1. The generation of ozone reduces the concentration of oxygen inside the substantially closed room 1 from 20.5% to about 18%. This reduction in oxygen concentration lowers the cellular metabolism of both the natural perishable products and the pathogenic organisms. In addition the oxidative character of the ozone has a bacteriostatic and fungistatic effect in the short term, followed by a bacteriocidal and fungicidal effect. These effects combine with the lowered metabolism to reduce ripening, retard spoilage and thus preserve the natural perishable products.

The method of the preferred embodiment of the invention was used to treat various varieties of fruits, resulting in the data indicated in Tables 1 to 4. There is no limitation on the type of natural perishable products that can be preserved using the present invention. The natural perishable products simply need to be placed in the substantially closed room 1 in such a way that they are exposed to the atmosphere. The packaging of the natural perishable product should also be chosen with the knowledge that the greater the exposure to the atmosphere within the substantially closed room, the greater the preservative effect of the present invention.

Figure 2:
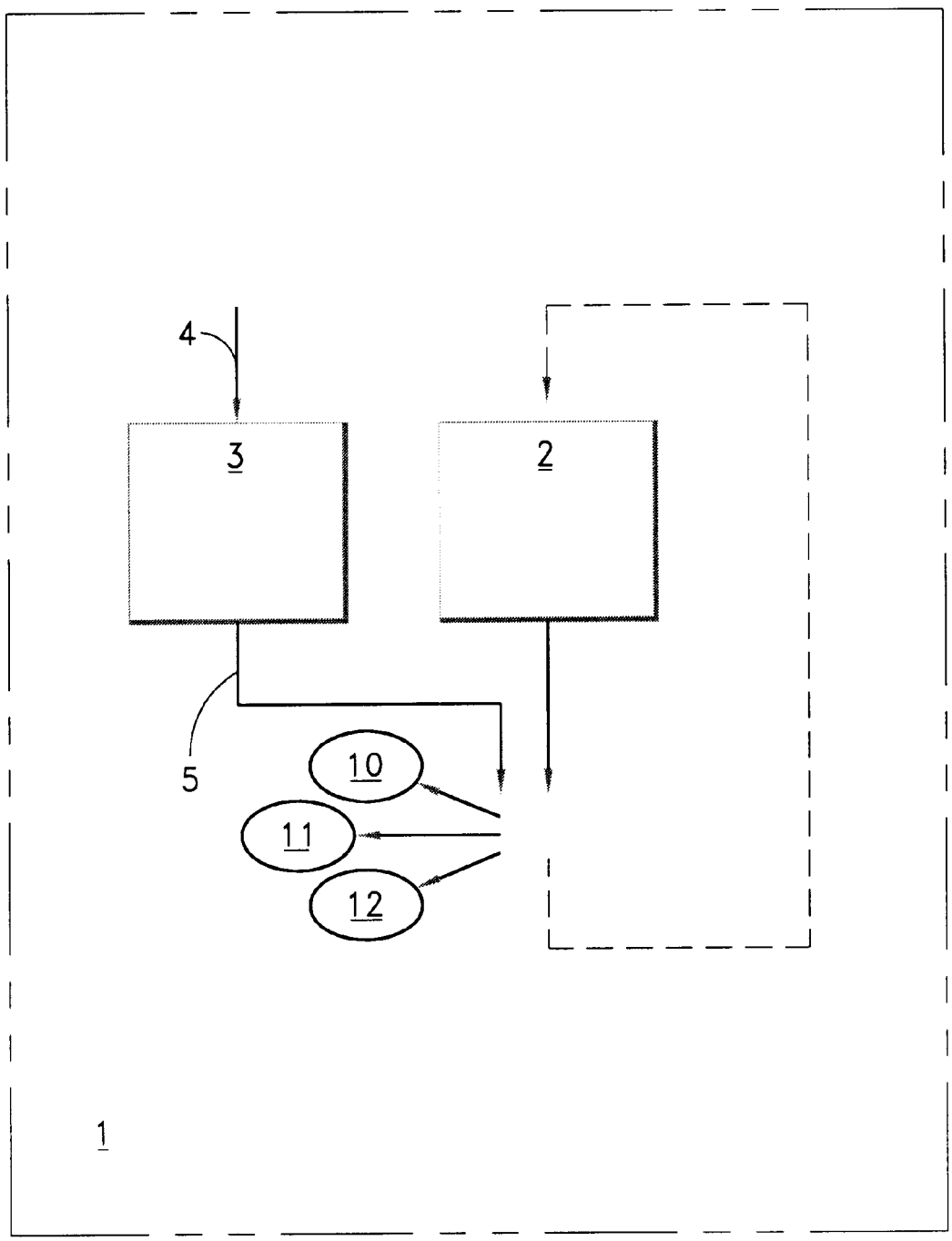
FIG. 2 shows a block diagram of another embodiment of the invention.

A second embodiment of the method of the present invention is illustrated in FIG. 2. This second embodiment is substantially similar to the embodiment illustrated and explained above for FIG. 1. However, this second embodiment also includes sensors for determining the temperature 10, humidity 11 and ozone concentration 12 of the air in the substantially closed room 1.

The ozone generating means 3 is installed inside the substantially closed room 1. However, the controls are installed outside of the substantially closed room 1, near the door, so that the ozone generating means 3 can be operated without entering the substantially closed room 1. Because the ozone generating means 3 runs on electricity, it is necessary to install electrical lines into the substantially closed room 1. In addition, the ozone generating means 3 must be chosen so that its capacity to produce ozone is appropriate for the size of the substantially closed room 1. Several modular models available commercially from Interozone, S.A. are capable of producing ozone from air using the corona discharge method. These are shown in Example 1. Similar ozone generating means from other manufacturers would also be appropriate for use in the method of the present invention. These alternative ozone generating means may use a different method of producing ozone from air.

| MODEL | WEIGHT (KG) | DIMENSIONS (MM) | CAPACITY (M³) |
| --- | --- | --- | --- |
| XES-125 | 10.5 | 600 × 500 × 300 | 300 |
| XES-245 | 12.0 | 600 × 500 × 300 | 450 |
| XES-365 | 21.0 | 900 × 500 × 390 | 600 |
| XES-485 | 31.5 | 950 × 500 × 390 | 1000 |
| XES-485R | 38.0 | 950 × 500 × 390 | 1800 |

The level of ozone maintained in the substantially closed room 1 may vary from as low as 0.02 PPM to as high as 0.5 PPM. One skilled in the art will realize that the optimum level will be determined based on the types of natural perishable products being treated and that some products may emit volatile compounds that effect ozone levels. Further, one skilled in the art will recognize that the levels of ozone maintained in the substantially closed room may be limited by governmental regulation. For example, OSHA regulations stipulate that eight hours of exposure to 0.1 PPM ozone is acceptable and that fifteen minutes of exposure to 0.3 PPM ozone is acceptable. Use of higher concentrations may be dangerous. In the preferred embodiment, the level of ozone will be maintained in accordance with governmental regulations. A constant level of ozone has provided consistently good results. Thus in order to maintain a controlled atmosphere with a constant level of ozone, personnel will not be permitted to regularly enter the substantially closed room 1.

The temperature of the substantially closed room 1 will vary depending on the types of natural perishable products being preserved. For example, the temperature may range from 0° C. for apples to 12° C. for bananas. The ozone generating means 3 is capable of being operated within the range of temperatures appropriate for preserving natural perishable products. Additionally, within this range there is no effect of temperature on the ratio of ozone to oxygen within the substantially closed room 1.

What is claimed is:

1. A method of preserving natural perishable products comprising:
    a) placing said natural perishable products in the interior of a substantially closed room containing air;
    b) generating ozone inside the substantially closed room from the oxygen in the air inside the substantially closed room by corona discharge; and
    c) dispersing the ozone throughout the substantially closed room.

2. The method of claim 1 in which an ozone generator is used to generate ozone inside the substantially closed room, said ozone generator comprising at least one entrance for air that feeds to said ozone generator from the interior of the substantially closed room and at least one exit in the interior of the substantially closed room for the ozone generated.

3. The method of claim 2 in which an air conditioning system of the closed cycle type is operated in the substantially closed room, said air conditioning system comprising entrances for air to be conditioned and air exits for conditioned air, said entrances and exits being disposed to take in and liberate, respectively, the air inside said substantially closed room.

4. The method of claim 3 in which at least one exit from said ozone generator is disposed next to an exit of said air conditioning system in a manner which mixes the ozone with the conditioned air.

5. The method of claim 4 wherein the mixture of ozone and conditioned air is distributed throughout the substantially closed room by the action of a blower.

6. The method of claim 3 in which said air conditioning system comprises a cooling system.

7. The method of claim 3 in which said air conditioning system comprises a heating system.

8. The method of claim 3 wherein said air conditioning system comprises a humidification system.

9. The method of claim 1, additionally comprising maintaining one or more characteristics of the room within a preselected range, said characteristics being selected from the group consisting of temperature, humidity and ozone concentration.

10. A method of preserving natural perishable products comprising:
    a) placing said natural perishable products in the interior of a substantially closed room containing air;
    b) reducing the level of oxygen in the substantially closed room to about 18% by generating ozone from the oxygen in the air inside the substantially closed room; and
    c) dispersing the ozone throughout the substantially closed room.

11. A method of preserving natural perishable products comprising:
    a) placing said natural perishable products in the interior of a substantially closed room containing air and comprising a closed-circuit air conditioning system;
    b) generating ozone from the oxygen in the air inside the substantially closed room; and
    c) dispersing the ozone throughout the substantially closed room by mixing the ozone with conditioned air being supplied to the room from the air conditioning system.

* * * * *

UNITED STATES PATENT AND TRADEMARK OFFICE
CERTIFICATE OF CORRECTION

PATENT NO.    : 6,503,547 B1
DATED         : January 7, 2003
INVENTOR(S)   : Carlos Lima It is certified that error appears in the above-identified patent and that said Letters Patent is hereby corrected as shown below:

<u>Title page,</u>
Item [75], correct the spelling of the inventor's name to read -- Carlos Lima --.

Signed and Sealed this

Thirteenth Day of May, 2003

JAMES E. ROGAN
*Director of the United States Patent and Trademark Office*